(12) United States Patent
Clerc et al.

(10) Patent No.: US 6,267,775 B1
(45) Date of Patent: *Jul. 31, 2001

(54) SELF-EXPANDING MEDICAL DEVICE FOR CENTERING RADIOACTIVE TREATMENT SOURCES IN BODY VESSELS

(75) Inventors: Claude O. Clerc, Eden Prairie; Jon S. Stinson, Plymouth, both of MN (US)

(73) Assignee: Schneider (USA) Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/519,521

(22) Filed: Mar. 6, 2000

Related U.S. Application Data

(63) Continuation of application No. 09/035,954, filed on Mar. 6, 1998, now Pat. No. 6,059,812.
(60) Provisional application No. 60/041,342, filed on Mar. 21, 1997.

(51) Int. Cl.[7] .................................................. A61M 29/00

(52) U.S. Cl. .............................................. 606/198; 600/3

(58) Field of Search ........................... 606/198, 191, 606/195, 194; 600/1, 3; 623/1.1, 1.16, 1.2

(56) References Cited

U.S. PATENT DOCUMENTS

| 2,546,761 | 3/1951 | Loftus | 128/1.2 |
| 2,862,108 | 11/1958 | Meilink | 250/106 |

(List continued on next page.)

FOREIGN PATENT DOCUMENTS

| WO 99/22812 | 5/1999 | (WO) . |
| WO 99/22815 | 5/1999 | (WO) . |

(List continued on next page.)

OTHER PUBLICATIONS

Tjho–Heslinga et al., "Results of ruthenium irradiation of uveal melanona", *Radiothereapy Oncology*, vol. 29, pp. 33–38, 1993.

Lommatzsch et al., "Radiation effects on the optic nerve observed after brachytherapy of choroidal melanomas with 106Ru/106Rh plaques", *Graefe's Arch. Clin Exp. Ophthalmology* vol. 232, pp. 482–487, 1994.

*Radiotherapy of Intraculare and Orbital Tumors*, Springer–Verlak publishers, Berlin Heidelberg and New York, copyright 1993, pp. 23–30 and 363–367.

Fackelmann, "Harbinger of a Heart Attack", *Science News*, vol. 151, Jun. 14, 1997, pp. 374–375.

Raloff, "Nuclear Medicine Gets Frienlier—Experimental Therapies Seek to Posion Just the Disease", *Science News*, vol. 152, Jul. 19, 1997, pp. 40–41.

Sutherland, "Managing Cancer Through Synergy", *Administrative Radiology Journal*, Nov. 1996, pp. 21–27.

*Primary Examiner*—Kevin Truong
(74) *Attorney, Agent, or Firm*—Crompton, Seager & Tufte, LLC

(57) ABSTRACT

A medical device for treating a body vessel with a radioactive source includes an elongated tubular catheter and an axially flexible support structure on a distal end of the catheter. The catheter has proximal and distal ends, and a lumen for receiving a radioactive source. The support structure is formed from a plurality of filaments which are helically wound and interwoven in a braided configuration and has a plurality of alternately spaced unconstricted and constricted regions. The unconstricted regions are radially compressible and self-expandable from a positioning diameter when the device is in a positioning state to a vessel-engaging, treatment diameter which is greater than the positioning diameter when the device is in the treatment state. The constricted regions are engaged with the catheter and concentric with the unconstricted regions. When in the treatment state the support structure causes the catheter to be substantially radially centered within a vessel so radiation is uniformly applied to the vessel during treatment.

18 Claims, 1 Drawing Sheet

U.S. PATENT DOCUMENTS

| | | | |
|---|---|---|---|
| 2,955,208 | 10/1960 | Stevens | 250/108 |
| 3,060,924 | 10/1962 | Rush | 128/1.2 |
| 3,147,383 | 9/1964 | Prest | 250/108 |
| 3,324,847 | 6/1967 | Zoumboulis | 128/1.2 |
| 3,505,991 | 4/1970 | Hellerstein et al. | 128/1.1 |
| 3,643,096 | 2/1972 | Jeffries, Jr. et al. | 250/108 R |
| 3,669,093 | 6/1972 | Sauerwein et al. | 128/1.1 |
| 3,674,006 | 7/1972 | Holmer | 128/1.2 |
| 3,750,653 | 8/1973 | Simon | 128/1.2 |
| 3,811,426 | 5/1974 | Culver et al. | 128/1.2 |
| 3,861,380 | 1/1975 | Chassagne et al. | 128/1.2 |
| 3,866,050 | 2/1975 | Whitfield | 250/497 |
| 3,927,325 | 12/1975 | Hungate et al. | 250/435 |
| 4,096,862 | 6/1978 | DeLuca | 128/348 |
| 4,220,864 | 9/1980 | Sauerwein et al. | 250/497 |
| 4,225,790 | 9/1980 | Parsons, Jr. et al. | 250/497 |
| 4,244,357 | 1/1981 | Morrison | 128/1.2 |
| 4,281,252 | 7/1981 | Parsons, Jr. et al. | 250/497 |
| 4,314,157 | 2/1982 | Gaines | 250/497 |
| 4,364,376 | 12/1982 | Bigham | 128/1.1 |
| 4,584,991 | 4/1986 | Tokita et al. | 128/1.1 |
| 4,588,395 | 5/1986 | Lemelson | 604/59 |
| 4,631,415 | 12/1986 | Sauerwein et al. | 250/497.1 |
| 4,655,771 | 4/1987 | Wallsten | 623/1 |
| 4,702,228 | 10/1987 | Russell, Jr. et al. | 128/1.2 |
| 4,706,652 | 11/1987 | Horowitz | 128/1.2 |
| 4,732,152 | 3/1988 | Wallsten et al. | 128/343 |
| 4,763,642 | 8/1988 | Horowitz | 128/1.2 |
| 4,763,671 | 8/1988 | Goffinet | 128/786 |
| 4,782,834 | 11/1988 | Maguire et al. | 128/344 |
| 4,784,116 | 11/1988 | Russell, Jr. et al. | 128/1.2 |
| 4,815,449 | 3/1989 | Horowitz | 600/7 |
| 4,819,618 | 4/1989 | Liprie | 600/7 |
| 4,851,694 | 7/1989 | Rague et al. | 250/497.1 |
| 4,861,520 | 8/1989 | van't Hooft et al. | 252/644 |
| 4,881,937 | 11/1989 | van't Hooft et al. | 600/3 |
| 4,897,076 | 1/1990 | Puthawala et al. | 600/7 |
| 4,936,823 | 6/1990 | Colvin et al. | 600/7 |
| 4,963,128 | 10/1990 | Daniel et al. | 600/7 |
| 4,969,863 | 11/1990 | van't Hooft et al. | 600/3 |
| 4,976,266 | 12/1990 | Huffman et al. | 128/659 |
| 4,976,680 | 12/1990 | Hayman et al. | 600/7 |
| 4,976,690 | 12/1990 | Solar et al. | 604/96 |
| 5,026,337 | 6/1991 | Burton et al. | 606/108 |
| 5,030,194 | 7/1991 | Van't Hooft | 600/3 |
| 5,032,113 | 7/1991 | Burns | 604/96 |
| 5,059,166 | 10/1991 | Fischell et al. | 600/3 |
| 5,061,275 | 10/1991 | Wallsten et al. | 623/1 |
| 5,084,001 | 1/1992 | Van't Hooft et al. | 600/3 |
| 5,084,002 | 1/1992 | Liprie | 600/7 |
| 5,092,834 | 3/1992 | Bradshaw et al. | 600/7 |
| 5,103,395 | 4/1992 | Spako et al. | 364/413.26 |
| 5,106,360 | 4/1992 | Ishiwara et al. | 600/2 |
| 5,120,973 | 6/1992 | Rohe et al. | 250/497.1 |
| 5,139,473 | 8/1992 | Bradshaw et al. | 600/3 |
| 5,141,487 | 8/1992 | Liprie | 600/7 |
| 5,147,282 | 9/1992 | Kan | 600/1 |
| 5,163,896 | 11/1992 | Suthanthiran et al. | 600/8 |
| 5,176,617 | 1/1993 | Fischell et al. | 600/3 |
| 5,183,455 | 2/1993 | Hayman et al. | 600/7 |
| 5,199,939 | 4/1993 | Dake et al. | 600/3 |
| 5,201,757 | 4/1993 | Heyn et al. | 606/198 |
| 5,213,561 | 5/1993 | Weinstein et al. | 600/7 |
| 5,267,960 | 12/1993 | Hayman et al. | 604/106 |
| 5,282,781 | 2/1994 | Liprie | 600/3 |
| 5,302,168 | 4/1994 | Hess | 600/7 |
| 5,344,383 | 9/1994 | Liping | 600/3 |
| 5,354,257 | 10/1994 | Roubin et al. | 600/7 |
| 5,370,685 | 12/1994 | Stevens | 623/2 |
| 5,391,139 | 2/1995 | Edmundson | 600/7 |
| 5,395,300 | 3/1995 | Liprie | 600/3 |
| 5,405,309 | 4/1995 | Carden, Jr. | 600/3 |
| 5,409,015 | 4/1995 | Palermo | 128/772 |
| 5,411,466 | 5/1995 | Hess | 600/3 |
| 5,425,720 | 6/1995 | Rogalsky et al. | 604/198 |
| 5,429,582 | 7/1995 | Williams | 600/2 |
| 5,484,384 | 1/1996 | Fearnot | 600/3 |
| 5,484,444 | 1/1996 | Braunschweiler | 606/108 |
| 5,498,227 | 3/1996 | Mawad | 600/3 |
| 5,503,613 | 4/1996 | Weinberger | 600/3 |
| 5,503,614 | 4/1996 | Liprie | 600/7 |
| 5,532,122 | 7/1996 | Drukier | 435/5 |
| 5,538,494 | 7/1996 | Matsuda | 600/1 |
| 5,540,659 | 7/1996 | Teirstein | 604/104 |
| 5,556,389 | 9/1996 | Liprie | 604/264 |
| 5,575,749 | 11/1996 | Liprie | 600/3 |
| 5,605,530 | 2/1997 | Fischell et al. | 600/3 |
| 5,611,767 | 3/1997 | Williams | 600/2 |
| 5,616,114 | 4/1997 | Thornton et al. | 600/3 |
| 5,618,266 | 4/1997 | Liprie | 604/21 |
| 5,624,372 | 4/1997 | Liprie | 600/3 |
| 5,643,171 | * 7/1997 | Bradshaw et al. | 600/3 |
| 5,649,924 | 7/1997 | Everett et al. | 606/15 |
| 5,653,683 | 8/1997 | D'Andrea | 604/21 |
| 5,662,580 | 9/1997 | Bradshaw et al. | 600/3 |
| 5,674,177 | 10/1997 | Hehrlein et al. | 600/3 |
| 5,683,345 | 11/1997 | Waksman et al. | 600/3 |
| 5,688,220 | 11/1997 | Verin et al. | 600/1 |
| 5,707,332 | 1/1998 | Weinberger | 600/3 |
| 5,713,828 | 2/1998 | Coniglione | 600/7 |
| 5,720,717 | 2/1998 | D'Andrea | 604/21 |
| 5,722,984 | 3/1998 | Fischell et al. | 606/198 |
| 5,728,042 | 3/1998 | Schwager | 600/3 |
| 5,730,698 | 3/1998 | Fischell et al. | 600/3 |
| 5,782,740 | * 7/1998 | Schneiderman | 600/1 |
| 5,782,742 | 7/1998 | Crocker et al. | 600/3 |
| 5,795,286 | 8/1998 | Fischell et al. | 600/3 |
| 5,800,333 | 9/1998 | Liprie | 600/3 |
| 5,803,895 | 9/1998 | Kronholz et al. | 600/3 |
| 5,807,231 | 9/1998 | Liprie | 600/3 |
| 5,816,259 | 10/1998 | Rose | 128/898 |
| 5,816,999 | 10/1998 | Bischoff et al. | 600/3 |
| 5,820,553 | 10/1998 | Hughes | 600/426 |
| 5,833,593 | 11/1998 | Liprie | 600/3 |
| 5,840,008 | 11/1998 | Klein et al. | 600/3 |
| 5,840,009 | 11/1998 | Fischell et al. | 6000/3 |
| 5,840,064 | 11/1998 | Liprie | 604/96 |
| 5,843,163 | 12/1998 | Wall | 623/1 |
| 5,851,171 | 12/1998 | Gasson | 600/3 |
| 5,851,172 | 12/1998 | Bueche et al. | 600/7 |
| 5,855,546 | 1/1999 | Hastings et al. | 600/3 |
| 5,857,956 | 1/1999 | Liprie | 600/7 |
| 5,863,284 | 1/1999 | Klein | 600/3 |
| 5,863,285 | 1/1999 | Coletti | 600/3 |
| 5,865,720 | 2/1999 | Hastings et al. | 600/3 |
| 5,871,436 | 2/1999 | Eury | 600/3 |
| 5,871,437 | 2/1999 | Alt | 600/3 |

FOREIGN PATENT DOCUMENTS

| | | |
|---|---|---|
| WO 99/24116 | 5/1999 | (WO) . |
| WO 99/24117 | 5/1999 | (WO) . |
| WO 99/29354 | 6/1999 | (WO) . |
| WO 99/29370 | 6/1999 | (WO) . |
| WO 99/29371 | 6/1999 | (WO) . |
| WO 99/30779 | 6/1999 | (WO) . |
| WO 99/34969 | 7/1999 | (WO) . |
| WO 99/36121 | 7/1999 | (WO) . |
| WO 99/39628 | 8/1999 | (WO) . |
| WO 99/40962 | 8/1999 | (WO) . |
| WO 99/40970 | 8/1999 | (WO) . |
| WO 99/40971 | 8/1999 | (WO) . |

| | | | | | |
|---|---|---|---|---|---|
| WO 99/40972 | 8/1999 | (WO). | WO 99/49935 | 10/1999 | (WO). |
| WO 99/40973 | 8/1999 | (WO). | WO 99/56825 | 11/1999 | (WO). |
| WO 99/40974 | 8/1999 | (WO). | WO 99/56828 | 11/1999 | (WO). |
| WO 99/42162 | 8/1999 | (WO). | WO 99/61107 | 12/1999 | (WO). |
| WO 99/42163 | 8/1999 | (WO). | WO 99/62598 | 12/1999 | (WO). |
| WO 99/42177 | 8/1999 | (WO). | WO 99/66979 | 12/1999 | (WO). |
| WO 99/44686 | 9/1999 | (WO). | | | |
| WO 99/44687 | 9/1999 | (WO). | | | |

* cited by examiner

SELF-EXPANDING MEDICAL DEVICE FOR CENTERING RADIOACTIVE TREATMENT SOURCES IN BODY VESSELS

REFERENCE TO RELATED APPLICATION

This application is a continuation of U.S. patent application Ser. No. 09/035,954, filed Mar. 6, 1998, which now U.S. Pat. No. 6,059,812, claims the benefit of U.S. Provisional Application Ser. No. 60/041,342 filed on Mar. 21, 1997.

FIELD OF THE INVENTION

The present invention relates generally to medical devices for positioning radioactive treatment sources in body vessels of patients. In particular, the present invention is a radially compressible and self-expandable device for centering radioactive treatment sources in body vessels.

DESCRIPTION OF THE RELATED ART

Medical devices configured for radiation treatments of stenosis (constricted regions) in blood flow-supporting and other vessels of a patient are generally known and disclosed, for example, in European Patent Publication No. 0 633 041 and German Patent Registration No. G 91 02 312.2. In general, the devices shown in these publications include an elongated flexible catheter tube with a radially expandable support structure such as a self-expandable stent or one or two inflatable balloons on its distal end. The devices are percutaneously inserted into the vessel and transluminally directed to the treatment site. After the support structure is located adjacent to the treatment site it is radially expanded to generally center the catheter tube within the vessel. A radioactive source is then inserted into and directed through the catheter tube until it is located at the treatment site. Following the treatment the radioactive source is withdrawn through the catheter. The support structure is then radially compressed or collapsed and the catheter tube withdrawn.

The intensity of radiation applied to the body tissues by sources typically used in these treatments varies nonlinearly with the distance of the source from the tissue (i.e., the intensity~$d^2$). To uniformly treat the tissue, it is therefore important for the radioactive source to be radially centered within the vessel at the treatment site. When used to treat linear vessel sections, the known support structures are generally capable of centering the radiation source to achieve a relatively uniform distribution of radiation at the treatment site. However, when these support structures are positioned at treatment sites in curved vessel sections, the catheter tube can be bent to a radius of curvature which is different than the curvature of the vessel section. Portions of the catheter tube, and therefore the radioactive source when positioned in the tube during treatment, will therefore be closer to one side of the vessel than the other. As a result, the dose of radiation applied to the treatment site may not be uniform.

It is evident that there is a continuing need for improved support structures for use in connection with radiation treatments of stenosis. In particular, there is a need for support structures capable of relatively accurately centering the radioactive source at treatment sites in curved vessel portions. The support structure should be capable of being accurately positioned, and relatively easily inserted and withdrawn. A device of this type which enables radiation treatments while allowing significant perfusion (flow) of blood through the vessel would be particularly advantageous.

SUMMARY OF THE INVENTION

The present invention is a medical device including a radioactive source within a support structure for treating a body vessel. The support structure of the device is capable of relatively accurately centering the source within a curved portion of a body vessel during radioactive treatments of stenosis. The support structure can be relatively easily positioned and withdrawn from the vessel, and allows blood perfusion during the treatments.

The support structure is an axially flexible member formed from a plurality of filaments which are helically wound and interwoven in a braided configuration. The support structure includes a plurality of spaced unconstricted regions and a plurality of spaced constricted regions. The unconstricted regions are radially compressible and self-expandable from a positioning diameter when the device is in a positioning state to a vessel-engaging, treatment diameter which is greater than the positioning diameter when the device is in a treatment state. The constricted regions are concentric with the unconstricted regions and have a diameter which is less than the treatment diameter of the unconstricted regions when the device is in the treatment state. The radioactive source is supported within the constricted regions of the support structure when the device is in the treatment state.

DETAILED DESCRIPTION OF THE PREFERRED EMBODIMENTS

Figure 1:
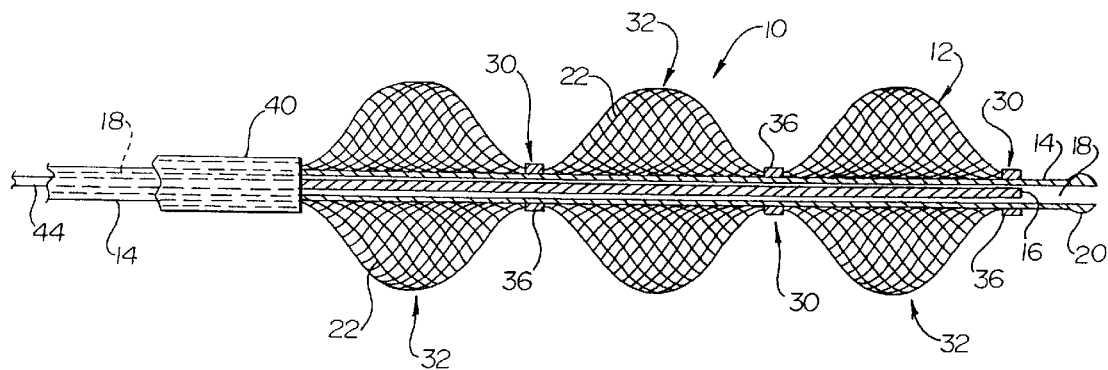
FIG. 1 is an illustration of a radioactive stenosis treatment device in accordance with the present invention in its treatment state.

A radioactive stenosis treatment device 10 in accordance with the present invention is illustrated in FIG. 1. As shown, the distal end of device 10 includes a support structure 12 concentrically mounted on the distal end of a tubular catheter 14, and a radioactive source 16 positioned within the catheter adjacent to the support structure. Catheter 14 is an elongated and axially flexible member having a lumen 18 and a tip 20 on its distal end. Catheter 18 will typically be fabricated from polymers such as polyethylene, PEEK (polyetheretherketones) and PTFE (polytetrafluoroethylene). The support structure 12 is an axially flexible member which is circular in cross section and formed from two sets of oppositely-directed, parallel, spaced-apart and helically wound elongated strands or filaments 22. The sets of filaments 22 are interwoven in an over and under braided configuration intersecting at points to form an open mesh or weave construction. Methods for fabricating members such as support structure 12 are generally known and disclosed, for example, in the Wallsten U.S. Pat. No. 4,655,771 and the Wallsten et al. U.S. Pat. No. 5,061,275, which are hereby incorporated by reference in their entirety for all purposes.

In a preferred embodiment the filaments 22 of support structure 12 are formed from relatively radiotransparent polymers such as Kevlar aramid fibers. Other radiotransparent polymers such as nylon and polyester can also be used. In still other embodiments filaments 22 are formed from relatively radiopaque polymers and metal alloys. For example Elgiloy® alloy from Carpenter Technology Corporation of Reading Pennsylvania and Phynox® alloy from Metal Imphy of Imphy, France can be used for filaments 22.

Support structure 12 includes a plurality of alternating and spaced constricted regions 30 and unconstricted regions 32. In the embodiment shown in FIG. 1, the constricted and unconstricted regions 30 and 32, respectively, are sections of a unitary braided structure of the type described above. The constricted regions 32 are formed by mounting the structure to the catheter tube 14 by expansion limiting members such as bands 36. Bands 36 can be formed from radiotransparent polymer or metal. Although the embodiment of support structure 12 shown in FIG. 1 has three unconstricted regions 32 and five constricted regions 30, other embodiments can have more or less constricted and unconstricted regions.

Support structure 12 is shown in its expanded or relaxed state in FIG. 1, i.e., in the configuration it assumes when subjected to no external loads or stresses. The filaments 22 are resilient, permitting the radial compression of the unconstricted regions 32 into a reduced-radius, extended-length configuration or state. The unconstricted regions 32 are self-expandable from the compressed state, and axially flexible. Constricted regions 30 are effectively engaged with the catheter 14, and are therefore concentric with the unconstricted regions 32. In its expanded state the support structure 12 has a generally sinusoidal shape with the unconstricted regions 32 forming lobes and the constricted regions 30 forming nodes. The diameter of the lobes of the unconstricted regions 32 slope from a relaxed or treatment diameter to a smaller positioning diameter at the constricted regions 30.

In other embodiments (not shown), support structure 12 is formed by positioning a unitary braided structure of the type described above on a mandrel (not shown) having the sinusoidal or other desired relaxed-state shape of the structure. The braided structure is then heated (e.g., to between about 500°–600° C., and preferably 550°) for a period of time (e.g., for between about one to four hours. and preferably three hours). This heat-treating process causes the support structure 12 to have a relaxed-state shape corresponding to that of the mandrel. The shaped support structure 12 is then mounted to the catheter 14 by conventional techniques such as adhesives or mechanical fasteners.

Figure 2:
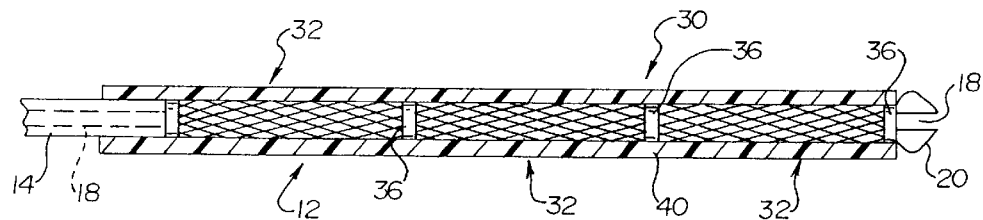
FIG. 2 is an illustration of the treatment device shown in FIG. 1 in its reduced-radius positioning state.

Conventional or otherwise known devices for delivering self-expanding stents can be used to deliver treatment device 10. Delivery devices of these types are, for example, disclosed in the Wallsten U.S. Pat. No. 4,732,152, Burton et al. U.S. Pat. No. 5,026,337, Heyn et al. U.S. Pat. No. 5,201,757 and Braunschweiler et al. U.S. Pat. No. 5,484,444. Briefly, as shown in FIG. 2, the delivery devices include an outer sheath 40 which extends over and surrounds the support structure 12 and constrains the support structure in its reduced-radius (i.e., positioning diameter) compressed or positioning state around the catheter 14. A deployment mechanism (not shown) which can be actuated from the proximal end of the delivery device retracts the outer sheath 40 with respect to the catheter 14, thereby allowing the support structure 12 to self-expand into its treatment state in engagement with with the inner wall of the vessel in which it is positioned (i.e., the unconstricted regions 32 self-expand to a treatment diameter).

Figure 3:
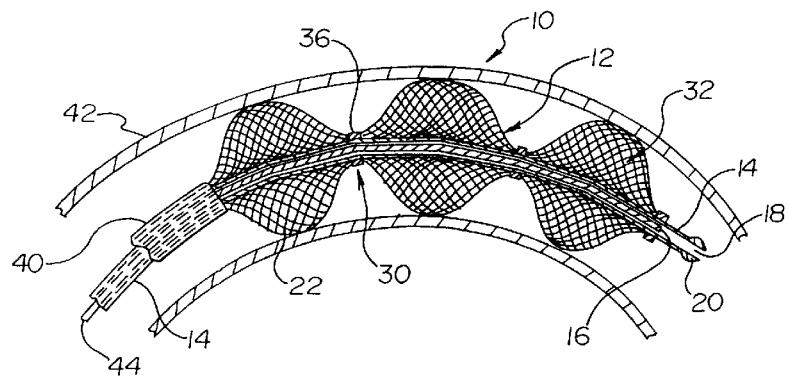
FIG. 3 is an illustration of the treatment device shown in FIG. 1 in its treatment state positioned within a body vessel.

When in its positioning state the assembled treatment device 10 is inserted percutaneously into a body vessel and directed through the vessel until the distal end of the constrained support structure 12 is positioned at the stenosis to be treated. The deployment mechanism is then actuated to retract the outer sheath 40 and allow the support structure to self-expand into its treatment state in engagement with the vessel. FIG. 3 is an illustration of the support structure 12 in its treatment state in a curved section of a vessel 42. As shown, the unconstricted regions 32 engage the vessel 42 at a number of spaced locations. Since the constricted regions 30 are concentric with the unconstricted regions 32, the constricted regions support the catheter 14 at a substantially radially centered position within the vessel 42. Radioactive source 16, which is on the distal end of a flexible shaft 44, is inserted into and directed through the lumen 18 of the catheter 14 until it is positioned in the support structure 12 at the treatement site. After the radioactive treatment the source 16 is withdrawn from the catheter 14. The deployment mechanism is then actuated to extend the outer sheath 40 and constrain the support structure 12 back into its reduced-radius positioning state, thereby enabling the treatment device 10 to be withdrawn from the vessel.

Any of a wide range of conventional or otherwise known radioactive sources 16, including beta and gamma emitters, can be used with treatment device 10. Examples of pure beta radiation emitting sources include Yttrium-90. Strontium-90, Phosphorous-32, Calcium-45 and European-169. Examples of gamma radiation emitting sources include Cobalt-60 and Iridium-192.

Radioactive treatment devices in accordance with the present invention offer a number of important advantages. Perhaps most importantly, the device can substantially radially center a radioactive source within curved and other sections of vessels being treated. The relatively porous nature of the support structure permits substantial blood perfusion during the treatments. The device can be relatively easily inserted, deployed and removed. It also can be positioned to a relatively high degree of accuracy.

Although the present invention has been described with reference to preferred embodiments, those skilled in the art will recognize that changes can be made in form and detail without departing from the spirit and scope of the invention.

What is claimed is:

1. A centering catheter for centering a radiation source in a vascular lumen, comprising:
   an elongate shaft having a proximal end and a distal end; and
   an expandable braid support structure connected to the distal end of the elongate shaft for centering the radioactive source within the vascular lumen, the braid structure defining a plurality of constriction regions upon expansion, the braid comprising a plurality of interwoven radio-transparent fibers.

2. A centering catheter as in claim 1, wherein the elongate shaft includes a source lumen extending therethrough which is adapted to accommodate the radioactive source therein.

3. A centering catheter as in claim 1, wherein the constricted regions are formed by constriction bands.

4. A centering catheter as in claim 1, wherein the constricted regions are formed by heat treating the braid.

5. A centering catheter as in claim 1, wherein the fibers comprise polymer fibers.

6. A centering catheter as in claim 5, wherein the polymer fibers comprise aramid fiber filaments.

7. A centering catheter as in claim 1, wherein the braid support structure is self-expanding.

8. A centering catheter as in claim 7, further comprising a tubular member disposed about the catheter and the expandable braid from retaining the braid in a collapsed configuration.

9. A medical system for treating a vascular site with ionizing radiation via a vascular lumen, comprising:
   an elongate radiation source; and a centering catheter for centering the radiation source in the vascular lumen, the centering catheter including an elongate shaft having a proximal end, a distal end and a source lumen extending therethrough which is adapted to accommodate the radioactive source therein, an expandable braid support structure connected to the distal end of the elongate shaft for centering the radioactive source within the vascular lumen, the braid structure defining a plurality of constriction regions upon expansion, the braid comprising a plurality of interwoven radio-transparent fibers.

10. A medical system as in claim 9, wherein the constricted regions are formed by constriction bands.

11. A medical system as in claim 9, wherein the constricted regions are formed by heat treating the braid.

12. A medical system as in claim 9, wherein the fibers comprise polymer fibers.

13. A medical system as in claim 12, wherein the polymer fibers comprise aramid fiber filaments.

14. A medical system as in claim 9, wherein the braid support structure is self-expanding.

15. A medical system as in claim 14, further comprising a tubular member disposed about the catheter and the expandable braid from retaining the braid in a collapsed configuration.

16. A centering catheter for centering a radiation source in a vascular lumen, comprising:

an elongate shaft having a proximal end, a distal end a source lumen extending therethrough which is adapted to accommodate the radioactive source therein;

an expandable braid support structure connected to the distal end of the elongate shaft for centering the source lumen and radioactive source within the vascular lumen, the braid comprising a plurality of interwoven radio-transparent polymer fibers; and a plurality of spaced apart constriction members disposed on the braid support structure for defining a plurality of constricted regions along the braid support structure when the braid is expanded.

17. A centering catheter as in claim 16, wherein the braid support structure is self-expanding.

18. A centering catheter as in claim 17, further comprising a tubular member disposed about the catheter and the expandable braid from retaining the braid in a collapsed configuration.

\* \* \* \* \*